United States Patent [19]

Rademacher

[11] Patent Number: 5,140,710
[45] Date of Patent: Aug. 25, 1992

[54] BILAYER X-RAY EYE SHIELD

[76] Inventor: Mark Rademacher, 3222 Royal Dr., Suite 5, Cameron Park, Calif. 95682

[21] Appl. No.: 577,318

[22] Filed: Sep. 4, 1990

[51] Int. Cl.$^5$ .............................................. A61F 9/02
[52] U.S. Cl. ........................................ 2/432; 2/426; 2/454; 351/44; 250/515.1; 250/516.1; 359/360; 359/738
[58] Field of Search ................ 2/2.1 A, 15, 426, 431, 2/432, 433, 434, 439, 454; 351/44; 250/515.1, 516.1; 350/1.6, 1.7, 410, 448

[56] References Cited

U.S. PATENT DOCUMENTS

| | | |
|---|---|---|
| 1,285,226 | 11/1918 | King . |
| 2,419,917 | 4/1947 | Robeson . |
| 3,030,628 | 4/1962 | Crosson . |
| 3,264,272 | 8/1966 | Rees . |
| 3,325,825 | 6/1967 | Christianson et al. . |
| 3,507,566 | 4/1970 | Knapp ..................................... 2/431 |
| 3,867,020 | 2/1975 | Braunhut . |
| 4,021,862 | 5/1977 | Glasser et al. . |
| 4,024,405 | 5/1977 | Szot . |
| 4,045,125 | 8/1977 | Farges ..................................... 351/44 |
| 4,070,097 | 1/1978 | Gelber ..................................... 351/44 |
| 4,129,524 | 12/1978 | Nagai et al. . |
| 4,182,821 | 1/1980 | Nagai et al. . |
| 4,386,277 | 5/1983 | Forshee ........................... 250/516.1 |
| 4,771,179 | 9/1988 | Ijiri et al. ........................... 250/515.1 |
| 4,793,002 | 12/1988 | Simon . |
| 4,795,654 | 1/1989 | Teleki ............................... 250/515.1 |
| 4,835,796 | 6/1989 | Wiedner ................................... 2/431 |
| 5,015,864 | 5/1991 | Maleki ............................... 250/515.1 |
| 5,016,292 | 5/1991 | Rademacher ........................... 2/431 |

FOREIGN PATENT DOCUMENTS

| | | |
|---|---|---|
| 894916 | 8/1949 | Fed. Rep. of Germany . |
| 2841484 | 4/1980 | Fed. Rep. of Germany .......... 2/431 |
| 146097 | 12/1978 | Japan ............................... 250/515.1 |
| 2068711 | 2/1981 | United Kingdom . |
| 2086210 | 11/1981 | United Kingdom . |

Primary Examiner—Werner H. Schroeder
Assistant Examiner—Michael A. Neas
Attorney, Agent, or Firm—James M. Ritchey

[57] ABSTRACT

An eye shield having two layers of X-radiation protective material is disclosed. X-radiation initially encounters a metalized thin layer that permits the substantial transmission of accompanying visible light yet partially diffracts, reflects, and refracts the X-radiation to decrease the amount of X-radiation passing through this metalized layer. Beneath the metalized thin layer is a lead layer that allows the passage of limited amounts of visible light yet functions to absorb effectively X-radiation. In combination, these two layers protect the eyes of a wearer from harmful X-radiation while permitting the wearer limited forward vision.

14 Claims, 4 Drawing Sheets

BILAYER X-RAY EYE SHIELD

BACKGROUND OF THE INVENTION

1. Field of the Invention

A bilayer protection device for shielding the eyes of a user from X-radiations is disclosed. More particularly, the present invention relates to a combined metalized thin layer diffractor/refractor/reflector and lead layer shield that together block a significant portion of incoming X-radiation from striking the eye tissue of a wearer while permitting the wearer limited forward vision.

Persons subjected to limited (short term exposure) or excessive (long term or repeated exposures) X-radiation may manifest eye damage. Primarily this damage is in the form of tumors and nuclear or cortical lens cataracts. Damage to an eye begins at the time of the X-ray exposure and continues to occur for several weeks thereafter, due to the generation of free radical toxins in the eye tissue during or after the X-radiation exposure.

In particular, individuals at risk include, but are not limited to, dental patients undergoing various preventative or treatment programs such as: C.T. scans, fluoroscopic studies, tomographic, cephalometric, panagraphic, full mouth series, bite wing, and occlusal X-ray procedures. Additionally, medical patients subjected to similar procedures are at risk as are the dental and medical personnel performing such manipulations. Further, persons found in any X-radiation containing environment might find the subject device useful for blocking X-rays while still retaining a narrowed forward vision.

2. Description of the Background Art

Historically, various X-radiation shielding devices have been presented to the public. Concerning versatility and effectiveness, these devices have numerous drawbacks. Many of the prior inventions are excessively heavy, too bulky or cumbersome for convenient utilization or use in areas with restricted space, too costly to produce, too complex to manufacture economically or to easily use, or generally fail to provide sufficiently for a wearer's reduced, but still existent, visual necessities while eliminating X-radiation.

Disclosed in U.S. Pat. No. 1,285,226 are eye protection goggles having two layers that resist shattering. One layer is optical quality material and the other layer is for structural stability with a small opening for viewing.

U.S. Pat. No. 2,419,917 relates to a vision aid. To reduce the brightness of the sun or surrounding lights, a device is produced that admits a limited amount of light through slit openings.

An anti-ray eye shield is depicted in U.S. Pat. No. 3,030,628. A series of hinged louvred openings in a face mask admit decreased levels of radiation by closing.

U.S. Pat. No. 3,325,825 discloses radio frequency shielding goggles and helmet. All openings are covered with screen and the remainder of the goggles has an electrically conducting film or other conducting material to introduce the shielding qualities.

A controlled light limiting lens assembly is described in U.S. Pat. No. 3,867,020. A louvred element having a central hole is positioned over a polarized element. By rotating the louvred element, any desired extraneous light, the angle of incidence of which is greater than the angle of the light accepted through the louvres, is blocked.

Presented in U.S. Pat. No. 4,021,862 is a radiation eye shield. This shield comprises lead-glass lenses and lead impregnated vinyl shielding for the surfaces surrounding the lenses.

U.S. Pat. No. 4,024,405 exhibits a X-ray shield having a radiolucent frame and radiopaque lens cup. Not only does the device prevent X-radiation from reaching a wearer, the device blocks visible light from reaching a wearer.

Protective eyewear is related in U.S. Pat. No. 4,793,002. An adjustably sized cone that does not transmit light is positioned over each eye of a wearer.

Polymer preparations are disclosed in U.S. Pat. Nos. 3,264,272, 4,129,524, and 4,182,821. These polymers may be employed to contain lead and thus serve as X-radiation blockers.

German Patent No. 894,916 shows a face mask that swings up during nonuse. U.K. Patent Application Nos. 2,068,711 and 2,086,210 disclose a protective face mask for protection from X-rays. The device encloses the entire face, most of the head, and the upper chest with lead or lead containing materials.

SUMMARY OF THE INVENTION

An object of the present invention is to produce an X-radiation eye protection shield that permits a wearer at least limited forward vision while effectively blocking harmful levels of X-radiation.

Another object of the present invention is to provide an improved X-radiation shield employing an initial layer containing metal, that diffracts, refracts, and reflects the X-rays and a secondary layer, containing lead, that primarily absorbs the X-rays.

An additional object of the present invention is to furnish a lightweight and easily manipulated X-radiation shield.

A further object of the present invention is to present a bilayered shield that effectively decreases the amount of transmitted X-radiation over that of a single layered lead shield while not significantly increasing the shield's overall weight by addition of the second non-lead layer.

Yet another object of the present invention is to produce a X-radiation shield that when sufficiently sealed or molded around its perimeter edge to a wearer's face to permit the wearer limited forward vision, decreased amounts of X-radiation pass under the sealed perimeter edge.

Still another object of the present invention is to provide a disposable holder for partially enclosing the two layers of the subject device, thereby decreasing the risk of propagating or transferring communicable diseases or agents.

The subject invention, a bilayer X-ray shield, comprises a first layer sufficiently transmissive to visible light for a wearer to have at least limited forward vision. Comprising the first layer is a thin metalized coating on a supporting polymer sheet. This layer functions as an X-radiation diffractor/refractor/reflector. Further comprising the bilayer shield is a second layer secured to the first layer between the first layer and the wearer. The second layer comprises an X-radiation absorptive lead body that is sufficiently transmissive to visible light for the wearer to have at least limited forward vision.

Other objects, advantages, and novel features of the present invention will become apparent from the detailed description that follows, when considered in conjunction with the associated drawings.

DESCRIPTION OF THE PREFERRED EMBODIMENT

Referring now to FIGS. 1-5, there are shown preferred embodiments of a visible light transmissive bilayer X-radiation shield 10 of the subject invention. The device is for effectively shielding a wearer's eyes (see "E" in FIG. 1 for a wearer's eye) from undesirable or harmful levels of X-radiation (see "X" in FIG. 1 for incoming X-rays) and may be incorporated into permanent or disposable versions comprising a bilayered shield having a first metalized coating layer and a second lead containing layer. Central to the functioning of the subject invention is this concept of the two layered X-radiation protective system. First, a film of thinly layered metal is deposited on a visible light transmissive supporting surface. This film of metal can be viewed as comprising successively layered parallel planes of metal atoms with an approximate repetitive planar spacing of "D". The deposited metal acts like a partial mirror for incoming X-rays whose wavelength is commensurate with the spacing "D" between the repetitive planes. As a result of this partially mirrored film, the X-radiation is not only diffracted, but refracted and reflected (and to a lesser extent absorbed). Since X-rays are both transmitted and refracted by the metalized coating layer, interference patterns (in accordance with wavefront splitting interferometer theory) are produced which direct scattered X-rays at divergent angles. The net result for the transmitted X-radiation is that the amount of X-rays that exits through the metalized film is less than the amount that initially struck that layer.

Further, a significant portion of the X-radiation that would have passed straight through a nonmetalized surface to encounter a subsequent lead containing layer (at least partially transmissive to visible light) is now angled, relative to a perpendicular to the lead containing layer's surface, after passage through the metalized film. Such angled X-rays have a longer pathlength through the second layer of lead containing material. The longer pathlength creates an increased probability of the X-radiation being absorbed by the lead, thereby further decreasing the level of X-rays exiting the second X-ray absorbing leaded layer and decreasing the required thickness of the heavy leaded layer.

Figure 1:
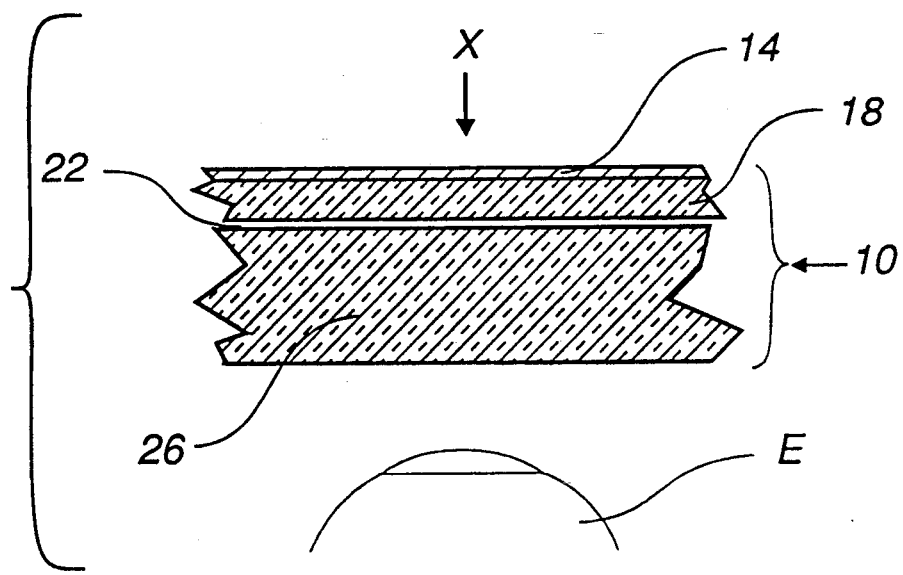
FIG. 1 is a cross sectional diagram showing the generalized components of the subject device in relation to incoming X-rays and a wearer's eye.

The subject invention, as illustrated in particular in FIG. 1, comprises a first layer of material that partially blocks X-radiation, but that is sufficiently transmissive to visible light to permit a wearer at least limited forward vision. The first layer includes a thin metalized coating 14. As indicated above, repeating layers of metal atoms can serve as partial mirrors for incident X-radiation, causing diffraction, refraction, and reflection to decrease the amount of X-rays transmitted through the first layer. Further, the thin metalized coating 14 serves as a diffractor/refractor/reflector of incoming X-radiation by having the spacings between successive layers of metal atoms approximately equal to the wavelength of the incoming X-radiation (e.g.; dental X-rays have wavelengths between 0.1 and 100 Angstroms). Since aluminum, chromium, and like metals (usually heavy metals having an atomic mass of greater than about 50 Daltons) are capable of diffracting, refracting, and reflecting X-radiation, when the spacing between planes of atoms are appropriate, these are suitable elements for the metalized coating 14. When such metals are applied to a distal surface of a supporting sheet 18 to generate a thin film coating 14 by standard techniques such as reactive sputter or vacuum metalization processes, the metallic layer's atomic interplanar spacing values are compatible with the X-ray wavelength distribution of about 0.1 to about 100 Angstroms. Thus, incident X-rays are diffracted by the metalized surface when they are reflected back from the first layer of metallic atoms, and by the layers beneath combining these reflections into a stationary interference pattern characteristic of the particular layer thickness. The thickness of the metal coating 14 (about 10 Angstoms to about 100 Angstroms or more) is such that X-radiation is diffracted, refracted, and reflected, but thin enough to pass at least enough visible light for the wearer to have limited vision of the surrounding environment.

The supporting sheet 18, having both a proximal surface and a distal surface, on which the metalized coating 14 is applied, generating the first layer, is of optically clear material that permits the transmission of visible light. Preferably, the supporting sheet 18 is a polymer material such as polyester, mylar, or similar substances that are not adversely or irreversibly altered by the metalization process that may involve heat, harsh chemicals, severe pressures, and the like. Usually, the supporting sheet 18 is flexible.

Immediately beneath the supporting sheet 18, associated with the sheet's proximal surface is an alignment or contact area 22. Area 22 is where the first layer encounters the second layer and may be an actual physical contacting of the two layers or an air gap between the two layers. Included is this area 22 are necessary adhesives for securing the two layers to one another, either proximate their outer edges or covering the entire area 22. If the adhesive covers a large portion of the contact area 22 and a wearer must see through the adhesive, the adhesive would need to be optically clear. It will be appreciated that the term adhesive includes means such as heating, pressurizing, and the like, in addition to actual adhesive compounds.

Abutting and secured to the alignment or contact area 22, between the first layer and the wearer, is the distal surface of the second lead containing body or layer 26. X-radiation is sufficiently absorbed by this leaded layer to the extent that about 90% or greater of the incoming X-rays do not reach the wearer's eyes. As indicated below, the composition of this leaded layer depends upon the exact version of the subject device 10. While severely restricting the passage of harmful levels of X-radiation, the second leaded layer is still partially transmissive to visible light and will permit a wearer at least limited forward vision. For example, should a dental patient be wearing the subject device 10, a dentist may want the patient to move according to visible hand signals. Further, when a patient wearing a mask or shield has at least some vision, that patient's tolerance to stressful situations is increased.

Figure 2:
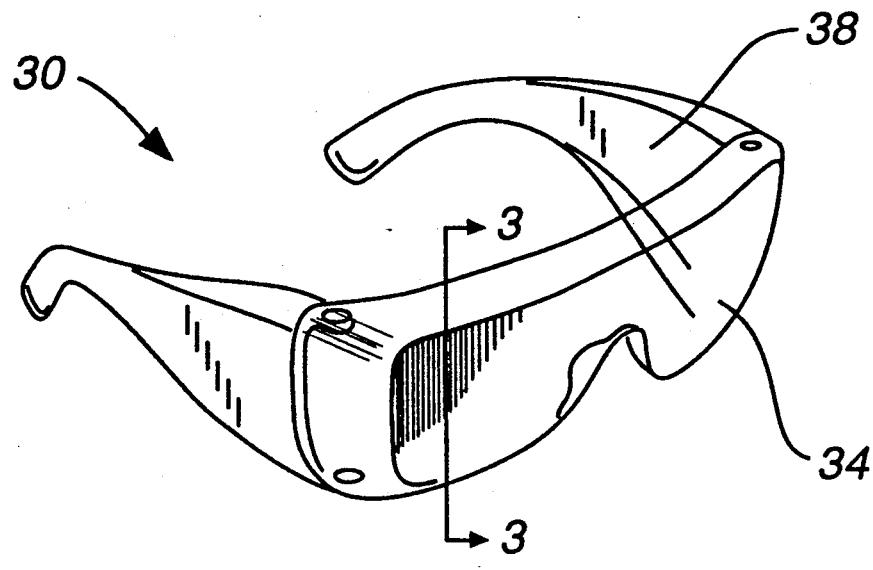
FIG. 2 is a perspective view of an embodiment of the subject device.
Figure 3:
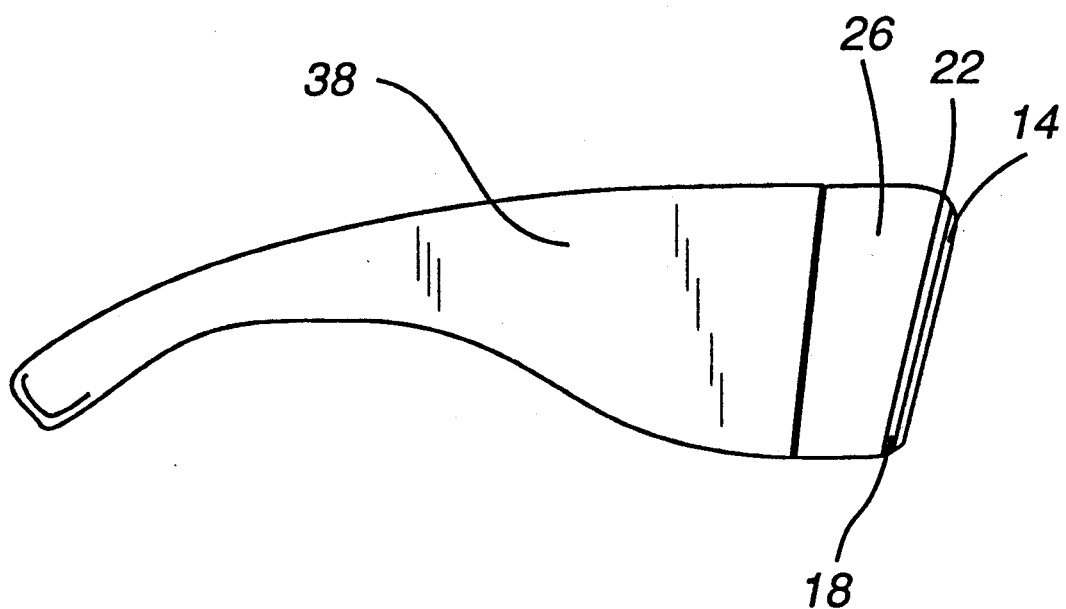
FIG. 3 is a cross sectional view of the embodiment shown in FIG. 2 taken along line 3—3.

FIGS. 2 and 3 are directed to one embodiment of the subject device 10. The subject device 10 is incorporated into a pair of safety goggles 30 comprising a protective bilayer shield 34 and earpieces 38. As seen in FIG. 3, the same subject components as generally pictured in FIG. 1 are present in the goggles 30. The metalized coating 14 is applied to the distal surface of the supporting sheet 18 and proximal surface of the supporting sheet 18 is secured to the second layer at the alignment area 22. In this goggles embodiment, the lead containing body 26 is specifically a leaded and essentially rigid lens. The leaded lens is essentially elongated (with a curve over the wearer's face that produces a convex hyperbolic mirror for the first layer's metalized coating that always reflects incoming X-rays away from a wearer's eyes) with a proximal surface, a distal surface, and a perimeter edge. The leaded lens is fabricated from either leaded glass or leaded polymer and is transmissive enough to visible light to permit a wearer at least limited forward vision. Preferably, to decrease the weight of the goggles, the leaded lens is a polymer construct. The leaded lens comprises is generally of uniform thickness usually from about 1 mm to about 9 mm, more preferably from about 2 mm to about 8 mm, and preferably about 7 mm. Suitable leaded lens materials comprise between about 20% and about 40% lead by weight. A preferred material for the construction of the lens is an acrylic polymer that contains 30% lead by weight. Although any suitably lead doped plastic polymer would be within the contemplation of this disclosure, a specific example is a 30% lead by weight acrylic copolymer known as CLEAR-Pb ® from Nuclear Associates (Nuclear Associates is a division of Victoreen, Inc., 100 Voice Road, Carle Place, N.Y. 11514-1593) which provides a lead thickness equivalence of about 0.3 mm of lead.

Generally, in manufacturing the goggles 30, first the metal coating 14 is applied to the supporting sheet 18. Second, the supporting sheet is secured to the leaded lens (lead containing body 26). Since the application of the metal coating 14 to the supporting sheet 18 usually involves severe conditions possibly harmful to the leaded lens, this order of assembly is preferred, but not required. Although not usually preferred, the metalized coating 14 may be applied directly on the distal surface of the leaded lens, thereby avoiding the supporting sheet 18.

No particular means for securing the goggles to a wearer is required, but preferably the means are earpieces 38 associated with the lens perimeter edge.

Figure 4B:
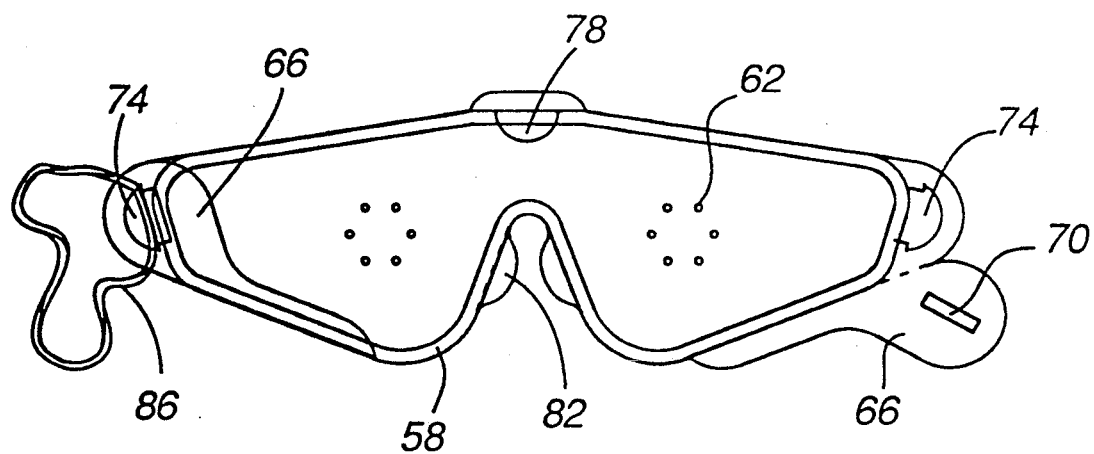
FIG. 4b is a front view of a further embodiment of the subject device showing a bilayer protection shield fitted within a disposable receiving holder.
Figure 4A:
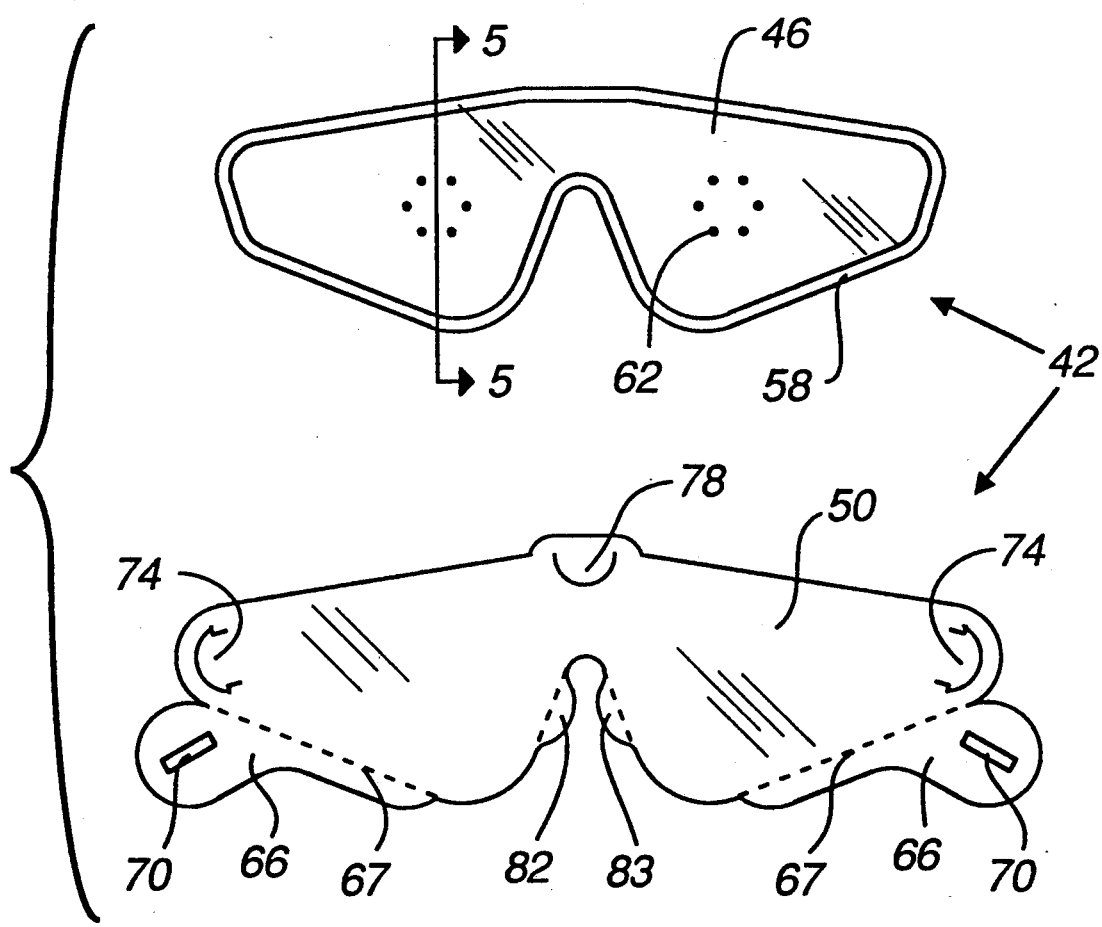
FIG. 4a is a front view of a further embodiment of the subject device showing a bilayer protection shield and a receiving holder.
Figure 5:
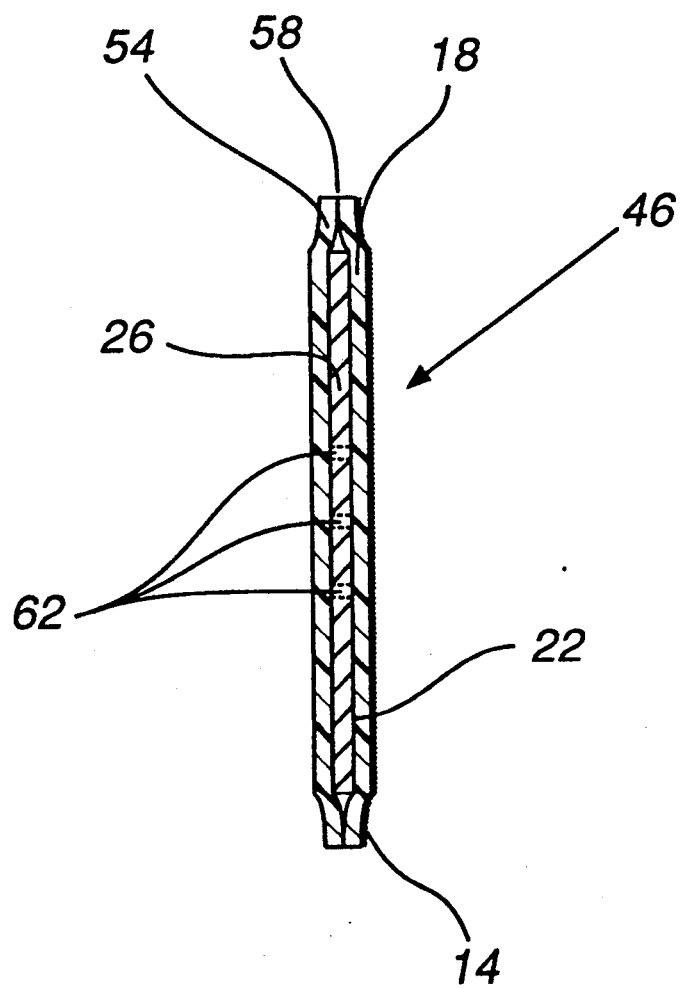
FIG. 5 is a cross sectional view of the bilayer protection shield shown in FIG. 4 taken along line 5—5.

FIGS. 4a, 4b, and 5 are directed to a further embodiment of the subject device 10. Depicted is a "disposable" shield 42 version of the bilayer invention. "Disposable" indicates that at least a portion of the subject shield may be thrown away after use by a wearer. This novel feature of the subject shield helps prevent the spread of communicable diseases from one wearer to another by permitting the disposal of the shield surface that contacts the wearer. Comprising the disposable shield is a bilayer shield component 46 and a disposable bilayer holder 50.

The bilayer shield component 46 comprises an elongated lead containing body 26 that is preferably a sheet of lead foil approximately 0.05 mm to about 1.0 mm in thickness, usually about 0.1 mm to about 0.25 mm, and preferably about 0.15 mm. As seen in particular in FIG. 5, the lead body 26 (the preferred sheet of lead foil having a distal surface, furthest from a wearer's face, and a proximal surface, closest to the wearer's face) comprising the second layer is sandwiched between the first layer (metalized coating 14 and supporting sheet 18) and a rear lead cover 54 and sealed at a joint 58 that runs the perimeter of the lead foil. The rear lead cover 54 is a material that is visible light transmissive polymer and is preferably fabricated of the same material as the supporting sheet 18. The main purpose of sealing the lead foil within a surrounding polymer skin or visible light transmissive protective wrapper is to prevent lead contamination of a wearer's or user's hands or other objects. The two polymer sheets (18 and 54) are sealed at joint 58 by standard methods including gluing, heating, and similar means.

Since the subject device shield must permit a wearer at least limited forward vision, the sheet of lead must be suitable modified to allow for this forward vision. Usually, a plurality of viewing apertures completely penetrate the lead sheet. It must be remembered that the number of apertures must be limited since each one permits not only light to pass, but also X-rays. As depicted in FIGS. 4a and 4b, preferably, a set of apertures, one set for each eye, are pinholes 62 arranged in a circular array (this could be viewed as a hexagonal outer perimeter) around a centrally located disk. Usually the diameter of the central array disk approximates one half the diameter of the human eye lens: 5.0 mm. The array diameter may vary with shielding requirements and may be as large as about 2 cm. The pictured hexagonal arrangement in lead foil (0.15 mm thick) results in over 90% reduction in direct X-ray beam cross sectional area which translates to less that 10% transmittance of X-radiation to a wearer's eyes. Further, an additional reduction in percentage transmittance ranging from about 0.1% to about 3.0% is estimated to occur with the utilization of the first layer (metalized coating) in conjunction with the second layer (lead sheet with the hexagonal array of apertures).

Two additional benefits result from employing small diameter aperture in a hexagonal array. First, by using standard Fourier optical theory of visible light, it is possible to calculate the convoluted point spread function (the image generated behind the shield which the eyes see) of the pinhole 62 or hexagonal array. The result is a hexagonal image array consisting of nineteen spots (twelve in an outer perimeter hexagon and six in an inner hexagon) of varying intensity with a bright nineteenth spot in the center (the center spot overlapping the iris of the eye and lens in the middle of the hexagonal array in the shield). This pattern allows for excellent visual imagery while providing a substantial lead barrier directly in the path of the incident X-rays.

Second, by having small diameter pinholes 62, it is clear from the Camera Obscura Principle that with such small apertures in the lead sheet that for a wearer to partially see through the shield it is necessary for contrast to exist between the lighted surroundings and a darkened zone beneath the shield in front of the wearer's eyes. To be most effective, the shield should seal over the wearer's eye area to form a preferably light excluded zone. This is achieved by applying fingertip pressure to the perimeter edge of the shield, thereby molding the soft lead sheet to the contours of the wearer's face. Once the sealing process has been completed, the darkened enclosure provides the necessary contrast for vision of the wearer's surroundings. A consequence of this process is that if adequate darkness is achieved to allow the viewing of images by a wearer, a relatively tight peripheral seal has been achieved and low angle X-ray scattering (at about 90° to the incident rays) are effectively shielded from the wearer.

The disposable bilayer holder 50 is preferably constructed from a single sheet of inexpensive (therefore disposable) visible clear polymer material (including plastics and like substances) that when forced into a fold tends to remain folded, but is essentially flexible unless forced into such a fold. Plainly other equivalent materials may be substituted for the preferred polymer material. Thus, when the lead sheet is molded to a wearer's face the holder 50 is likewise molded and held in that shape by the formed lead sheet.

The bilayer shield 46 is held within the holder 50 so that the first layer is distal to a wearer and the second layer is proximal to the wearer. The supporting sheet proximal surface overlays the lead sheet distal surface. This orientation is easily achieved when the first and second layers are surrounded within the above mentioned protective wrapper and the metalized coating is positioned away from the wearer and within the holder 50.

FIG. 4a shows the holder 50 in a flattened form, while FIG. 4b displays the holder 50 with one of its two flaps 66 folded up along flap fold line 67 (away from the face of a wearer) to generate a receiving pocket for perimeter of the bilayer shield 46 (both flaps 66 are folded up during actual use of the subject device). To secure each flap 66, two end slots 70 are present into which holder end tabs 74 fit. Further strengthening the holder's 50 grasp on the bilayer shield 46 is nose bridge tab 78 that slips over the top perimeter edge of the bilayer shield 46 (away from the face of the wearer). Two nose rests 82 are bent along nose rest fold lines 83 to provide support on the wearer's nose. As with the goggles 30 embodiment above, the disposable embodiment has means for securing or retaining the bilayer 46 and holder 50 to a wearer. Although equivalent means are contemplated to be within the realm of this disclosure, a simple elastic member or rubber band 86 is suitable for fitting under end tab 74 and over the wearer's ears.

Generally the disposable shield 42 would be distributed in kit form comprising a protectively wrapped bilayer shield 46 and a plurality of disposable holders 50 with wearer retention means 86. Since the holder 50 contacts a wearer's face, the holder 50 is discarded after each wearer is finished undergoing exposure to X-radiation.

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

What is claimed is:

1. A visible light transmissive bilayer shield for effectively blocking undesirable levels of X-radiation from striking the eye tissue of a wearer, comprising:
   a) a first layer sufficiently transmissive to visible light for said wearer to have at least limited forward vision comprising a thin metalized coating and
   b) a second layer secured to said first layer between said first layer and said wearer wherein said second layer is sufficiently transmissive to visible light for said wearer to have at least limited forward vision comprising a X-radiation absorptive lead containing body, wherein said lead containing body comprises a sheet of lead having a distal surface and a proximal surface and a plurality of viewing apertures completely penetrating said lead sheet.

2. A bilayer shield according to claim 1, further comprising a visible light transmissive protective wrapper surrounding said lead sheet.

3. A bilayer shield according to claim 1, further comprising a bilayer holder for containing said first and said second layers in an orientation wherein said first layer is held distal to said wearer and said second layer is held proximal to said wearer whereby said supporting sheet proximal surface overlays said lead sheet distal surface.

4. A bilayer shield according to claim 3, further comprising means associated with said bilayer holder for securing said shield over said wearer's eyes.

5. A bilayer shield according to claim 1, wherein said lead containing body comprises an essentially flattened and elongated leaded lens having a distal surface, a proximal surface, and a perimeter edge.

6. A bilayer shield according to claim 5, wherein said lens is fabricated from either leaded glass or leaded polymer.

7. A bilayer shield according to claim 5, wherein said first layer further comprises a visible light transmissive supporting sheet having both a distal surface and a proximal surface on which said metalized coating is applied to said supporting sheet distal surface and said supporting sheet proximal surface is secured to said distal leaded lens surface.

8. A bilayer shield according to claim 5, wherein said first layer metalized coating is applied directly on said distal leaded lens surface.

9. A bilayer shield according to claim 5, further comprising means associated with said lens perimeter for securing said shield to said wearer.

10. A visible light transmissive bilayer shield for effectively blocking undesirable levels of X-radiation from striking the eye tissue of a wearer, comprising:
    a) a first layer sufficiently transmissive to visible light for said wearer to have at least limited forward vision comprising a thin metalized coating applied to a distal surface of a visible light transmissive supporting polymer sheet having said distal surface and a proximal surface;
    b) a second layer sufficiently transmissive to visible light for said wearer to have at least limited forward vision comprising a X-radiation absorptive sheet of lead having a distal surface and a proximal surface and a plurality of viewing apertures completely penetrating said lead sheet; and
    c) a bilayer holder for containing said first and said second layers in an orientation wherein said first layer is held distal to said wearer and said second layer is held proximal to said wearer whereby said supporting sheet proximal surface overlays said lead sheet distal surface.

11. A bilayer shield according to claim 10, further comprising means associated with said bilayer holder for securing said shield over said wearer's eyes.

12. A bilayer shield according to claim 10, wherein said bilayer holder is disposable thereby decreasing the possibility of propagating a communicable agent from said wearer to another wearer.

13. A visible light transmissive bilayer shield for effectively blocking undersirable levels of X-radiation from striking the eye tissue of a wearer, comprising:

a) a first layer sufficiently transmissive to visible light for said wearer to have at least limited forward vision comprising a thin metalized coating applied to a distal surface of a visible light transmissive supporting polymer sheet having said distal surface and a proximal surface and b) a second layer sufficiently transmissive to visible light for said wearer to have at least limited forward vision comprising a X-radiation absorptive lead containing body wherein said lead containing body comprises an essentially flattened and elongated leaded lens having a distal surface, a proximal surface, and a perimeter edge whereby said supporting polymer sheet proximal surface is secured to said leaded lens distal surface.

14. A bilayer shield according to claim 13, further comprising means associated with said lens perimeter for securing said shield to said wearer.

* * * * *